United States Patent [19]

Carpino et al.

[11] Patent Number: 4,460,501
[45] Date of Patent: Jul. 17, 1984

[54] PROCESS FOR THE SYNTHESIS OF PEPTIDES UTILIZING THIOXANTHYLMETHYLOXYCARBONYL DIOXIDES

[75] Inventors: Louis A. Carpino, Amherst, Mass.; David Segev, D.N. Evtah, Israel

[73] Assignee: Research Corporation, Tuscon, Ariz.

[21] Appl. No.: 527,750

[22] Filed: Aug. 30, 1983

[51] Int. Cl.³ .............................................. C07G 7/00
[52] U.S. Cl. ........................ 260/112 R; 260/112.5 R; 549/27
[58] Field of Search .................... 260/112 R, 112.5 R; 549/27

[56] References Cited

U.S. PATENT DOCUMENTS 2,629,719  6/1947  Cusic ..................................... 549/27
4,350,627  9/1982  Castiglione et al. .......... 260/112.5 R Primary Examiner—John Kight, III
Assistant Examiner—Garnette D. Draper
Attorney, Agent, or Firm—Scully, Scott, Murphy & Presser

[57] ABSTRACT

A composition of the formula:

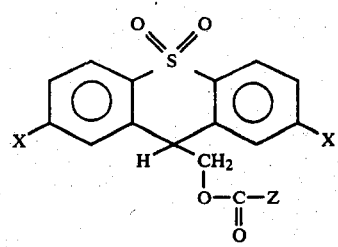

wherein X is lower alkyl, and Z is an amino acid a peptide residue or a good leaving group, the composition is adaptable as a blocking or protecting group for an amine composition useful in peptide synthesis and a method of protecting an amino group of an organic molecule during a reaction which modifies a portion of the molecule other than the protected amino group.

21 Claims, No Drawings

PROCESS FOR THE SYNTHESIS OF PEPTIDES UTILIZING THIOXANTHYLMETHYLOXYCARBONYL DIOXIDES

FIELD OF THE INVENTION

This invention relates to new thioxanthylmethyloxycarbonyl dioxide compounds and their use in peptide synthesis. More particularly, this invention relates to the use of these novel compounds as blocking groups which attach to amine groups to protect the amine group from undergoing undesirable side reactions during peptide synthesis.

BACKGROUND OF THE INVENTION

Support for the research leading to this invention was sponsored, in part, by the National Institute of Health, which support is gratefully acknowledged by the inventors.

Present methods exist by which an amino acid can be polymerized to yield polypeptides of high molecular weight. These products have been found to be useful as model compounds for both fibrous and globular proteins. Peptide synthesis also has application for the preparation of compounds identical with naturally occurring polypeptide compounds.

A basic problem in peptide synthesis is one of blocking or protecting the amino group from interaction with a carboxyl group on the same amino acid. These undesirable side reactions are prevented by attaching to one amino acid a group that will render the —NH$_2$ unreactive and to permit the desired reaction to take place. In addition to providing protection for the amino group, the blocking group is preferably one that can be easily removed without destruction of any peptide linkage that may have been built up during the synthesis. (See generally, Morrison and Boyd, *Organic Chemistry*, Third Ed., Sec. 36.10 Synthesis of Peptides, pp. 1147–1150 (1973)).

Previous work has been done to provide blocking compounds useful in peptide synthesis. Some of this work is reported, for example, by Carpino, et al.; *Journal of Organic Chem.*, Vol. 37, pp. 3404–3409 (1972); Kemp, et al., *Tetrahedron Letters*, Vol. 52, pp. 4629–4632 (1975); U.S. Pat. No. 4,267,344 to Halstrom, et al.; U.S. Pat. No. 4,159,979 to Fujino, et al. and U.S. Pat. Nos. 3,835,175 and 3,906,031 to Carpino, et al. The compounds reported in the above-cited references are of limited applicability because a deblocking reagent is generally required to remove these blocking compounds from the peptide. Use of a deblocking reagent can cause undesirable side reactions, can contribute to destruction of peptide linkages and recemization of the product.

It has now been found that certain thioxanthylmethyloxycarbonyl dioxides are effective blocking groups and undergo deblocking and cleavage by weak bases such as pyridine. More interestingly, these compounds have been shown to undergo deblocking simply upon standing at room temperature in certain dipolar aprotic solvents. Such deblocking under relatively mild conditions contributes to removal of the blocking group without destruction of peptide linkages that have been built up during polymerization and peptide synthesis.

SUMMARY OF THE INVENTION

It is therefore an object of the invention to provide novel compounds which act as effective blocking groups to protect an amino group from side reactions. It is a further object of the invention to provide novel compounds which are good protecting groups and are also easily cleaved from the reactive site when such blocking is no longer required.

It is an additional object of the invention to provide a method of protecting an amino group of an organic molecule during a reaction which modifies a portion of the molecule other than the protected amino group. It is further an object of the invention to provide a blocking group which effectively protects the anino group and is also efficiently and easily cleaved from the molecule to effect deblocking when desired.

Additional objects and advantages of the invention will be set forth, in part, in the description which follows and in part will be obvious from the description, or may be learned by practice of the invention. The objects and advantages of the invention are realized and obtained by means of the compounds, methods, processes and the combinations particularly pointed out in the appended claims.

To achieve the objects in accordance with the purposes of the invention, as embodied and broadly described herein, the invention comprises a composition of the formula

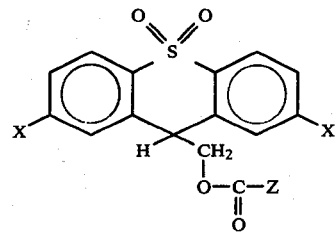

wherein X is a lower alkyl, and Z is a good leaving group or an amino acid or peptide residue.

In preferred embodiments of the invention, X is t-butyl and Z is an amino acid group. In a more preferred embodiment of the invention, Z is a polymer amino acid group. Most preferably, Z is a peptide or polypeptide group.

As embodied and broadly described herein, the invention also comprises a composition of the formula

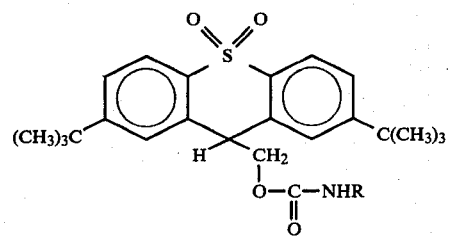

wherein NHR is an amino acid group and R is the residue of the amino acid group.

In a preferred embodiment of the invention the composition is a protected amine composition, whereby the NH of the amino acid group is protected from further reaction due to its bonding to thioxanthylmethyloxycarbonyl (TMOC) dioxide.

As embodied and broadly described herein, the invention also comprises a method for protecting an amino group of an organic molecule during a reaction which modifies a portion of the molecule other than the protected amino acid group. The method comprises the steps of (a) bonding a di-lower-alkyl-TMOC carbonyl derivative with an amine, thereby protecting said amine from further reaction; (b) modifying a portion of the organic molecule other than the protected amine, by chemical reaction in a suitable solvent system which forms a solvent/reaction mixture; and, (c) cleaving the protecting group from the amino group to deblock the amino group and produce an unprotected amine. In a preferred embodiment of the method of the invention, the modifying chemical reaction is carried out at room temperature in a solvent system in which deblocking of the protected amine does not readily occur at room temperature. The cleaving step comprises altering the solvent system upon completion of the reaction to effect deblocking of the amine from the protecting group. In a most preferred embodiment of the method of the invention, the solvent is a mixture of tetrahydrofuran and dimethyl sulfoxide, wherein the solvent mixture contains an amount of tetrahydrofuran effective to prevent the blocking of the amine during the modifying reaction step and deblocking occurs after removal of a sufficient amount of tetrahydrofuran from the reaction system.

It is to be understood that both the foregoing general and following detailed description are exemplary and explanatory only and are not intended to be restrictive of the invention as claimed.

DETAILED DESCRIPTION OF PREFERRED EMBODIMENTS OF THE INVENTION

Reference will now be made in detail to present preferred embodiments of the invention, examples of which are illustrated in the following example section.

In accordance with the invention, a composition of the formula:

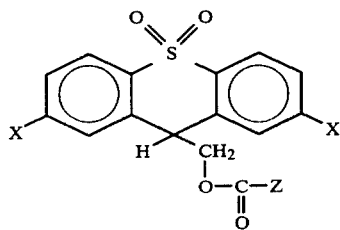

wherein X is lower alkyl, and Z is an amino acid or peptide residue or a good leaving group, is prepared. Preferably, X is t-butyl and Z is an amino acid group. More particularly, Z is a polymer amino acid group. In a more preferred embodiment, Z is a peptide group. In a most preferred embodiment, Z is a polypeptide group.

Z is a good leaving group in derivatives which are used to introduce the di-t-butyl TMOC function, such as for example in chloroformate derivative wherein Z=Cl. As is generally known in the art and for the purposes of the present invention "a good leaving group" is defined as a group which is readily broken away from its union with the carbon atoms. It is one which readily joins, for example, with an active hydrogen atom to split out a compound containing the hydrogen atom and the leaving group. Leaving groups are generallly electron attracting groups either because of their electro-negativity or because they have an inductive effect. When Z is an amino acid residue or a peptide residue it is not a good leaving group but becomes part of a stable system.

In accordance with the invention, the composition of the formula:

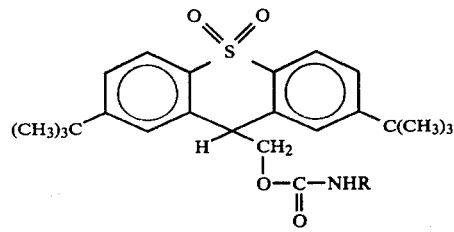

wherein NHR is an amino acid groups is prepared. In a preferred embodiment of the invention, the composition is a protected amine composition of the above formula, wherein NHR is an amino acid group, wherein the NH of the amino acid group is protected from further reaction due to its bonding to the TMOC dioxide. In a more preferred embodiment, the NHR is a peptide. In a most preferred embodiment, NHR is a polypeptide. In accordance with the invention, a method of protecting an amino group of an organic molecule during a reaction which modifies a portion of said molecule other than the protected amino group comprises the steps of:

(a) bonding a di-lower-alkyl-thioxanthylmethyloxycarbonyl derivative with an amine, thereby protecting the amine from further reaction;

(b) modifying a portion of the organic molecule other than the protected amine, by chemical reaction in a suitable solvent system which forms a solvent/reaction mixture; and (c) cleaving the protected group from the amino group to deblock the amino group and produce an unprotected amine.

Preferably, the modifying chemical reaction is carried out in a solvent system in which deblocking of the protected amine does not readily occur at room temperature.

More particularly, the modifying chemical reaction is carried out at room temperature (about 22°–24° C.) in a solvent system in which deblocking of the protected amine does not readily occur at such temperatures.

The cleaving step comprises altering the solvent system, upon completion of the modifying reaction, to effect deblocking of the amine and removal of the protecting group.

The solvent utilized is preferably dimethyl sulfoxide (DMSO). More preferably, the solvent is a mixture of tetrahydrofuran and DMSO.

If a DMSO solvent is utilized the deblocking of the amine from the protecting group is effected by altering the solvent system by slightly warming the solvent/reaction mixture from room temperature to above about 45° C., more preferably, to about 50° C.

Where the solvent mixture is tetrahydrofuran and DMSO, the tetrahydrofuran is present in an amount effective to prevent the blocking of the amine during the modifying reaction step. Preferably, the solvent mixture amounts of tetrahydrofuran to dimethyl sulfoxide is about 1:1 by volume at room temperature.

The deblocking of the amine from the protecting group can be effected by evacuating the solvent/reaction mixture to remove the tetrahydrofuran component of the solvent mixture and slightly warming the solvent/reaction mixture to above about 45° C.

The compositions of the invention are particularly advantageous to protect amino groups during modifying reactions because they are effective blocking groups and are easily cleaved from the reaction mixture, such as by slight warming of the reaction mixture when DMSO is used as a solvent. Other dipolar aprotic solvents such as dimethyl formamide (DMF) or dimethylacetamide (DMA) may be used to achieve similar results. Of particular advantage is the fact that deblocking does not occur in solvents such as DMSO if significant quantities of tetrahydrofuran (THF) are present. The presence of THF in DMSO in a molar ratio of 1:1 has been found to be effective to permit coupling reactions to be carried out with a significant margin of safety for deblocking not to occur. In order to effect deblocking, the THF can then be removed from the reaction mixture, by means such as evacuation and elevating the temperature of the reaction solution to slightly above room temperature wherein the blocking group insoluble in DMSO, will precipitate out. The reaction scheme can be shown as follows: wherein DBD-TMOC=di-t-butyl-TMOC; PNHR—OH=amino group containing compound to be protected; and H-CONH-R=a peptide compound:

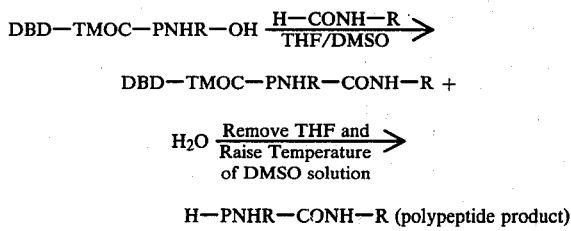

The compositions and methods of the invention are particularly applicable to methods of peptide synthesis. The compounds and methods of the invention may also be adaptable to semi-automatic methods of peptide synthesis, possibly in combination with polymeric active esters, as is well known in the art.

It is therefore apparent that the compounds and methods of the invention provide useful blocking compositions that are of particular use in peptide synthesis. The production of peptides and polypeptides are well known methods in the art and the utility of the compounds synthesized are also of well known utility.

EXAMPLES

The invention will now be illustrated by examples. The examples are not intended to be limiting of the scope of the present invention. In conjunction with the general and detailed description above, the examples provide further understanding of the present invention and outlines a synthesis of a preferred embodiment of the invention.

The following examples represent preferred embodiments of the compositions of the invention and methods for carrying out the blocking and deblocking of amides as can be applied to peptide and polypeptide synthesis. The starting materials for the examples whose method of preparation are not indicated, are commercially available compounds which would be available from chemical supply houses well known to the art such as Aldrich Chemical Co.

EXAMPLE 1

A chloroformate of TMOC dioxide of the invention is prepared according to the following synthesis sequence steps.

Step 1

Bis-(4-t-butylphenyl)-sulfide

To a mixture of 93 g of phenyl sulfide, 92.5 g of t-butyl chloride and 200 mL of $CS_2$ cooled in an ice bath, 133 g of $AlCl_3$ was added over a period of 1 hour. Following complete addition, the mixture was allowed to warm slowly to room temperature and stirred overnight. The mixture was subjected to decomposition with ice, extraction with ether and washing of the ether solution successively with water, 5% $NaHCO_3$, water and saturated NaCl solution and gave after evaporation of dried ($MgSO_4$) extracts, a solid which upon crystallization from methanol gave 145 g (97%) of the sulfide as white crystals, m.p. 83–84; $^1H$ NMR ($CDCl_3$) δ 1.32 (s, 18H, $CH_3$), 7.35 (s, 8H, aryl).

Step 2 2,7-Di-t-butylthioxanthenone

To a mixture of 12 g of bis-(4-t-butylphenyl)-sulfide, 100 mL of dry $CH_2Cl_2$ and 21 g of $SnCl_4$ cooled in an ice bath for a period of 30 min., a solution of 9.27 g of α,α-dichloromethyl methyl ether in 50 mL of $CH_2CH_2$ was added dropwise. After addition was complete, a deep red mixture was obtained which was allowed to warm slowly to room temperature, stirred for 2 hours and then slowly poured into water. Extraction with $CHCl_3$, followed by washing of the extracts successively with $H_2O$, 5% $NaHCO_3$, $H_2O$ and saturated NaCl solution, drying over ($MgSO_4$), and evaporation of solvent gave a red oil which was chromatographed on silica gel. Elution by means of hexane-ethyl acetate (95/5) removed 4.6 g (37% of 2,7-di-t-butylthioxanthene after which there was obtained 4.65 g (37%) of the ketone which was recrystallized from hexane—$CH_2Cl_2$ as yellow crystals, m.p. 176°–178°, $^1$NMR ($CDCl_3$) δ 1.35 (s, 18H, $CH_3$), 7.5 (m, 4H, aryl), 8.75 (d, 2H, CHCCO). Anal. calculated for $C_{21}H_{24}OS$: C, 77.73; H, 7.46; S, 9.88. Found C, 77.83; H, 7.58; S, 9.75.

Step 3

2,7-Di-t-butylthioxanthene

The red oil obtained as described above from 12 g of bis-(4-t-butylphenyl)-sulfide was dissolved in 100 mL of dry ether, and the solution added dropwise over 15 min. to a suspension of 2.5 g of lithium aluminum hydride in 100 mL of dry ether while cooling in an ice bath. The mixture was refluxed for 3 hours, cooled and excess hydride destroyed by means of saturated ammonium chloride solution. The ether layer was washed with $H_2O$ and saturated NaCl solution, dried over $MgSO_4$, and then evaporated to a white solid which was recrystallized from $CH_2Cl_2$-hexane to give 9.0 g (72%) of the thioxanthene as white crystals, m.p. 152°–154°, $^1$H NMR ($CDCl_3$) δ 1.28 (s, 18H, $CH_3$), 3.84 (s, 2H, $CH_2$), 7.31 (m, 6H, aryl). Anal. calculated for $C_{21}H_{26}S$: C, 81.23; H, 8.44; S, 10.33. Found: C, 81.45; H, 8.61; S, 10.24.

Step 4

2,7-Di-t-butylthioxanthen-9-yl methanol

To a solution of 15 g of 2,7-di-t-butylthioxanthene in 150 mL of dry THF cooled to −75°, mL of n-butyl lithium solution (2.45 M) was added dropwise. A deep red color developed. After stirring at −75° for 30 min., 5 g of paraformaldehyde was added slowly. The mixture was then allowed to warm to room temperature and refluxed for 30 min. Completion of the reaction was signaled by discharge of the red color. The mixture, which contained a gray precipitate, was cooled and decomposed with ice and 25% $H_2SO_4$. Extraction of the aqueous layer with $CH_2Cl_2$, followed by washing of the extracts with $H_2O$ and saturated NaCl solution, drying over ($MgSO_4$) and then evaporation gave an oily material which was purified by chromatography on silica gel by elution with hexane-ethyl acetate (95/5). The alcohol was obtained as a white solid, m.p. 158°–159°. Anal. calculated for $C_{22}H_{28}OS$: C, 77.64; H, 8.13; S, 9.41. Found: C, 77.72; H, 8.52; S, 9.28.

Step 5

2,7-Di-t-butyl-10,10-dioxythioxanthen-9-ylmethanol

To a solution of 10 g of 2,7-di-t-butylthioxanthenyl-9-methanol in 50 mL of acetic acid was added slowly 25 g of 30% $H_2O_2$ and the mixture was heated at 100° for 4 hours. Cooling, dilution with 200 mL of water and filtration gave 7 g of the crude sulfone. Recrystallization from $CH_2Cl_2$—hexane gave 6 g (55%) of the sulfone as white crystals, m.p. 200°–203°; $^1H$ NMR ($CDCl_3$ δ 1.25 (s, 18H, $CH_3$), 2.4 (br s, 1H, OH), 4.0 (m, 3H, $CHCH_2$), 7.5 (m, 4H, aryl), 8.0 (d, 2H, $CHCSO_2$).

Step 6

2,7-(Di-t-butyl-10,10-dioxythioxanthen-9-yl)methyl-N-p-chlorophenyl carbamate A solution of 1.1 g of 2,7-di-t-butyl-10,10-dioxythioxanthen-9-yl methanol and 0.41 g of p-chlorophenyl isocyanate in 15 ml of dry benzene was refluxed for 10 hours. Evaporation of solvent and recrystallization from $CH_2$—$Cl_2$—hexane gave a theoretical yield of the urethane as white crystals, m.p. 150°.

Step 7

2,7-Di-t-butyl-10,10-dioxythioxanthen-9-yl methyl chloroformate

To a solution of 5 g of phosgene in 150 mL of dry THF was slowly added, with stirring, 8.7 g of 2,7-di-t-butyl-10,10-dioxythioxanthen-9-yl methanol while cooling in an ice bath. The solution was then stirred in the ice bath for 2 hours and at room temperature for 4 hours. Excess phosgene was removed by a stream of $N_2$ and THF evaporated to a white solid which upon recrystallization from ether gave 8.85 g (87%) of the chloroformate as white crystals, m.p. 200°–201°, $^1H$ NMR ($CDCl_3$) δ 1.35 (s, 18H, $CH_3$), 4.7 (m, 3H, $CHCH_2$), 7.6 (m, 4H, aryl), 8.1 (d, 2H, $CHCSO_2$). Anal. calculated for $C_{23}H_{27}ClO_4S$: C, 63.51; H, 6.26; S, 7.37. Found: C, 63.68; H, 6.48; S, 7.08.

EXAMPLE 2

DBD-TMOC-Phe-OH

To a mixture of 1.2 g of L-phenylalanine in 20 mL of 10% $NaHCO_3$ and 20 mL of THF, cooled in an ice bath there was added slowly a solution of 3.5 g of 2,7-di-t-butyl-10,10-dioxythioxanthen-9-yl methyl chloroformate (DBD-TMOC-Cl) in 50 mL of THF. The mixture was stirred for 1 hour at 0°, 1 hour at room temperature, and then poured into 200 mL of water. Extraction with ether removed excess chloroformate and any alcohol that may have been formed. The aqueous layer was cooled to 0° and neutralized by slow addition of conc. HCl. The oily substance was extracted with $CH_2Cl_2$ and the organic phase washed with $H_2O$, saturated NaCl and then dried over $MgSO_4$. Evaporation of the solvent gave an oily product which after recrystallization from $CH_2Cl_2$ gave 4.18 g (96%) of the protected amino acid (DBD-TMOC-Phe-OH) 2,7-di-t-butyl-10,10-dioxythioxanthen-9-yl methyloxycarbonyl phenylalanine, m.p. 74°. Anal. calculated for $C_{32}H_{37}O_6NS$: C, 68.18; H, 6.61; S, 5.68. Found: C, 68.56; H, 6.92; S, 5.57.

EXAMPLE 3

DBD-TMOC-Gly-Gly-OH

Prepared as given for the phenylalanine derivative in 90% yield of 2,7-di-t-butyl-10,10-dioxythioxanthen-9-yl methyloxycarbonylglycylglycine (DBD-TMOC-Gly-Gly-OH), m.p. 74° after crystallization from $CH_2Cl_2$.

EXAMPLE 4

DBD-TMOC-Phe-Leu-OCMe₃

To a solution of 1.12 g of DBD-TMOC-Phe-OH in 25 mL of dry THF was added 0.352 of H-Leu-OCMe₃ and 0.385 g of dicyclohexylcarbodiimide. The mixture was stirred for 1 hour at −20° and then for 1 hour at room temperature. The mixture was filtered to remove dicyclohexylurea and the solvent evaporated under reduced pressure. The oily residue was chromatographed on silica gel with elution by ether-hexane (1:1). Removal of solvent gave an oil which was recrystallized from $CH_2Cl_2$ to give 1.41 g (94.6%) of the dipeptide ester 2,7-di-t-butyl-10,10-dioxythioxanthen-9-yl methyloxycarbonylphenylalanylleucine t-butyl ester (DBD-TMOC-Phe-Leu-OCMe₃), m.p. 79°. Anal. calculated for $C_{42}H_{56}N_2O_7S$: C, 68.85; H, 7.65; N, 3.82; S, 4.37. Found: C, 68.40; H, 8.02; N, 3.40; S, 4.37.

EXAMPLE 5

DBD-TMOC-Gly-Gly-Phe-Leu-OCMe₃

To a solution of 0.85 g of DBD-TMOC-Gly-Gly-OH in 20 mL of dry THF there was added 0.53 g of H-Phe-Leu-OCMe₃ and 0.38 g of dicyclohexylcarbodiimide. The mixture was stirred at 0° for 1 hour and at room temperature for 2 hours. The urea was filtered and the residue obtained after evaporation of the THF was chromatographed on silica gel using hexane-ethyl acetate (60/40) to give 1.21 g (89.6%) of the protected tetrapeptide ester 2,7-t-butyl-10,10-dioxythioxanthen-9-yl methyloxycarbonylglycylglycyl phenylalanyl leucine t-butyl ester (DBD-TMOC-Gly-Gly-Phe-Leu OC-Me₃), m.p. 150°.

EXAMPLE 6

Deblocking of DBD-TMOC-Phe-Leu-OCMe₃

A solution of 1.1 g of the protected dipeptide ester in 5 mL of DMSO was warmed to 50° for 40 min. during which time a precipitate of 10,10-dioxy-2,7-di-t-butyl-9-methylenethioxanthene separated. NMR examination showed that precipitation of the fulvene was complete, with none of this compound remaining in solution. In addition, no fulvene could be detected in the solution by thin layer chromatography (TLC). Filtration, followed by addition of water to the filtrate and extraction with ether, gave the dipeptide t-butyl ester, identified by spectral comparison (NMR, IR) with an authentic sample.

Other deblocking conditions were examined with DBD-TMOC-NHC$_6$H$_4$-Cl-p as a model urethane. At room temperature in DMSO for 6 hours deblocking occurred to the extent of 30% as shown by NMR analysis. At 75° in DMSO for 40 min. deblocking was complete. At room temperature in N,N-dimethylacetamide no deblocking was visible after 15 min. but after 60 min. 13.6% deblocking had occurred. In either DMSO-THF (1/1) or DMOS-CHCl$_3$ (1/3) no deblocking occurred after 16 hours.

EXAMPLE 7

10,10-Dioxy-2,7-di-t-butyl-9-methylenethioxanthene

Deblocking of any DBD-TMOC derivative in DMOS as described above gave an insoluble precipitate which was recrystallized from CH$_2$Cl$_2$ to give white crystals, m.p. 246°–248°. Anal. calculated for C$_{22}$H$_{26}$O$_2$S: C, 74.54; H, 7.39; S, 9.05. Found: C, 74.48; H, 7.61; S, 9.19.

As is noted from the above examples, the composition of the present invention and the method of deblocking can proceed without requiring the addition of base or other deblocking reagents to deblock or remove the blocking group. The absence of the base is particularly advantageous since the base may act upon the polypeptide chain and effect racemization of the amino acid residues contained therein.

The scope of the present invention is not limited by the description, examples, and suggested uses herein, and modifications can be made without departing from the spirit of the invention. For example, it may be noted that other alkyl derivatives of the TMOC dioxide such as methyl, ethyl and isopropyl TMOC dioxides may give fulvenes which are analogous to those preferred embodiments described above. Thus, it is intended that the present invention cover the modifications and variations of this invention provided they come within the scope of the appended claims and their equivalents.

What is claimed is:
1. A composition of the formula

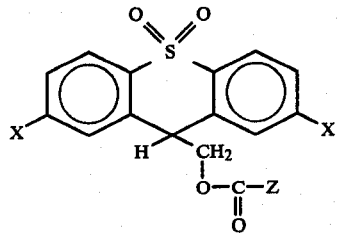

wherein X is lower alkyl, and Z is amino acid or peptide residue or a good leaving group.

2. The composition of claim 1 wherein X is butyl.
3. The composition of claim 1 wherein Z is an amino acid group.
4. The composition of claim 1 wherein Z is a polymer amino acid group.
5. The composition of claim 1 wherein Z is a peptide group.
6. The composition of claim 1 wherein Z is a polypeptide group.

7. A composition of the formula:

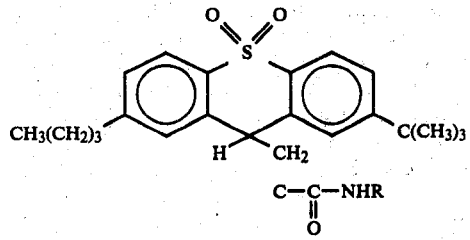

wherein NHR is an amino acid group and R is the residue of the amino acid group.

8. A protected amine composition of the formula:

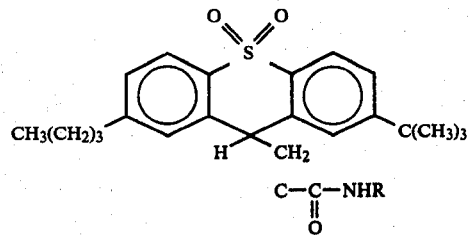

wherein NHR is an amino acid group wherein R is the residue of the amino acid group and the NH of the amino acid group is protected from further reaction due to its bonding to the thioxanthylmethyloxycarbonyl (TMOC) dioxide.

9. The protected amine composition of claim 1 wheren NHR is a peptide.
10. The protected amine composition of claim 9 wherein NHR is a polypeptide.
11. A method of protecting an amino group of an organic molecule during a reaction which modifies a portion of said molecule other than the protected amino group, comprising the steps of:
 (a) bonding a di-lower-alkyl-thioxanthylmethyloxycarbonyl derivatives with an amine, thereby protecting said amine from further reaction;
 (b) modifying a portion of the organic molecule other than the protected amine, by chemical reaction in a suitable solvent system which forms a solvent-/reaction mixture; and
 (c) cleaving the protecting group from the amino group to deblock the amino group and produce an unprotected amine.
12. The method of claim 1 wherein the modifying chemical reaction is carried out in a solvent system in which deblocking of the protected amine does not readily occur at room temperature.
13. The method of claim 12 wherein the cleaving step comprises altering the solvent system, upon completion of said reaction to effect deblocking of the amine from the protecting group.
14. The method of claim 12 wherein the modifying chemical reaction is carried out at room temperature (about 22°–24° C.) in a solvent system in which deblocking of the protected amine does not readily occur at room temperature and the cleaving step comprises altering the solvent system upon completion of said reaction to effect deblocking of the amine from the protecting group.
15. The method of claim 14 wherein the solvent is dimethyl sulfoxide (DMSO).

16. The method of claim 15 wherein the solvent is a mixture of tetrahydrofuran and dimethyl sulfoxide.

17. The method of claim 14 wherein the solvent is dimethyl sulfoxide (DMSO) and deblocking of the amine from the protecting group is effected by altering the solvent system by slightly warming the solvent/reaction mixture from room temperature (about 22°–24° C.) to above about 45° C.

18. The method of claim 17 wherein the solvent system is altered by slightly warming the solvent/reaction mixture from room temperature to about 50° C.

19. The method of claim 16 wherein the solvent mixture of tetrahydrofuran and dimethyl sulfoxide contains an amount of tetrahydrofuran effective to prevent deblocking of the amine during the modifying reaction step.

20. The method of claim 16 wherein the solvent mixture of tetrahydrofuran to dimethyl sulfoxide is about 1:1 by volume at room temperature.

21. The method of claim 19 wherein the deblocking of the amine from the protecting group is effected by evacuating the solvent/reaction mixture and slightly warming the solvent/reaction mixture to above about 45° C.

* * * * *